(12) United States Patent
Dinovo et al.

(10) Patent No.: US 12,257,310 B2
(45) Date of Patent: Mar. 25, 2025

(54) REACTIVE AND SORBENT MATERIALS

(71) Applicants: Dominic P. Dinovo, Dublin, OH (US); Andrew Dinovo, Columbus, OH (US); Matthew F. Smiechowski, Westerville, OH (US); Francis H. Verhoff, Cincinnati, OH (US)

(72) Inventors: Dominic P. Dinovo, Dublin, OH (US); Andrew Dinovo, Columbus, OH (US); Matthew F. Smiechowski, Westerville, OH (US); Francis H. Verhoff, Cincinnati, OH (US)

(*) Notice: Subject to any disclaimer, the term of this patent is extended or adjusted under 35 U.S.C. 154(b) by 0 days.

(21) Appl. No.: 15/789,941

(22) Filed: Oct. 20, 2017

(65) Prior Publication Data

US 2018/0110868 A1 Apr. 26, 2018

Related U.S. Application Data

(60) Provisional application No. 62/410,477, filed on Oct. 20, 2016.

(51) Int. Cl.
| | | |
|---|---|---|
| *A61K 47/61* | (2017.01) | |
| *A61K 9/00* | (2006.01) | |
| *A61K 9/14* | (2006.01) | |
| *A61K 35/74* | (2015.01) | |
| *A61K 36/062* | (2006.01) | |
| *A61K 38/47* | (2006.01) | |
| *A61K 47/69* | (2017.01) | |
| *C12N 11/02* | (2006.01) | |
| *C12N 11/06* | (2006.01) | |
| *C12N 11/10* | (2006.01) | |
| *C12N 11/14* | (2006.01) | |

(52) U.S. Cl.
CPC ............ *A61K 47/61* (2017.08); *A61K 9/0053* (2013.01); *A61K 9/146* (2013.01); *A61K 35/74* (2013.01); *A61K 36/062* (2013.01); *A61K 38/47* (2013.01); *A61K 47/6921* (2017.08); *C12N 11/02* (2013.01); *C12N 11/06* (2013.01); *C12N 11/10* (2013.01); *C12N 11/14* (2013.01); *C12Y 302/01017* (2013.01)

(58) Field of Classification Search
None
See application file for complete search history.

(56) References Cited

U.S. PATENT DOCUMENTS

| | | | | |
|---|---|---|---|---|
| 4,141,857 A | * | 2/1979 | Levy | .............. C12N 11/089 502/159 |
| 4,268,419 A | * | 5/1981 | Rohrbach | ............. C12N 11/082 502/7 |
| 9,944,920 B2 | * | 4/2018 | DiNovo | ................. C12N 11/02 |
| 2007/0104836 A1 | * | 5/2007 | Zhao | ................... A23C 19/063 426/61 |
| 2010/0078381 A1 | * | 4/2010 | Merchant | ........... B01D 67/0006 210/632 |
| 2012/0100203 A1 | * | 4/2012 | Fang | ..................... H01M 4/131 424/443 |
| 2014/0294839 A1 | * | 10/2014 | Kuret | ..................... C07K 16/18 424/139.1 |
| 2016/0089669 A1 | * | 3/2016 | Regnier | ................ B01L 3/5023 422/535 |
| 2016/0116476 A1 | * | 4/2016 | Takeichi | .............. G01N 21/293 435/6.11 |
| 2018/0073046 A1 | * | 3/2018 | Boeriu | .................. C12P 7/6418 |
| 2018/0110868 A1 | | 4/2018 | DiNovo et al. | |
| 2021/0113739 A1 | * | 4/2021 | Yang | ....................... A61L 27/48 |
| 2021/0196246 A1 | * | 7/2021 | Wang | .................. A61B 10/0051 |

FOREIGN PATENT DOCUMENTS

WO 2013071284 A1 5/2013

OTHER PUBLICATIONS

Xi et al. Process Biochemistry (2005) 40: 2833-2840 (Year: 2005).*
Lian et al. Process Biochemistry (2012) 47: 201-208 (Year: 2012).*
Elnashar et al., Novel Epoxy Activated Hydrogels for Solving Lactose Intolerance, Biomedical Research International, Jan. 2014, pp. 1-9, vol. 2014.
Haider et al., Concanavalin A Layered Calcium Alginate-Starch Beads Immoblized @ Galactosidase as a Therapeutic Agent For Lactose Intolerant Patients, International Journal of Pharmaceutics, Jul. 2008, pp. 1-6, vol. 359, Elsevier, NL.

* cited by examiner

*Primary Examiner* — Nghi V Nguyen
(74) *Attorney, Agent, or Firm* — Edward E. Sowers; Brannon Sowers & Cracraft PC

(57) ABSTRACT

Reactive and sorbent materials including a non-encapsulated crosslinked biological material immobilized on a support matrix that includes a polyamine and at least one support material are described. The support material can be an inorganic or organic support material. The reactive and sorbent materials are formed by reacting the biological material with the polyamine, at least one support material, and a crosslinking agent. The materials exhibit enhanced properties generally, are capable of maintaining their reactive and sorbent properties in contact with digestive fluids, and exhibiting their reactive and sorbent properties as they pass throughout an organism's entire digestive system. Reactive and sorbent materials in contact with digestive juices at pH's ranging from about 3 to about 7 have maintained their reactive and sorbent properties for at least 4 hours.

19 Claims, No Drawings

REACTIVE AND SORBENT MATERIALS

CROSS-REFERENCES TO RELATED APPLICATIONS

This application claims the benefit of U.S. Provisional Patent Application No. 62/410,477, filed Oct. 20, 2016 and entitled REACTIVE AND SORBENT MATERIALS, which is incorporated herein by reference.

TECHNICAL FIELD

The present invention relates to both reactive and sorbent (e.g. adsorbing, absorbing, etc.) crosslinked and supported biological components including but not limited to enzymes, microbial cell components and cells, antibodies, aptamers, DNA, and RNA, having increased or enhanced reactivity, increased or enhanced stability through digestive fluids and/or environments, increased and/or enhanced sorbency, and increased or enhanced functional properties throughout that exposure. Once immobilized as described herein, these biological components are stabilized to be passed through an animal's digestive system, with its low pH and the presence of protease and other digestive enzymes, without losing their functional properties. The claimed materials exhibit enhanced reactivities and enhanced stabilities when in contact with digestive fluids, and in other environments. The materials can be encapsulated or non-capsulated.

BACKGROUND

Crosslinked (sometimes referred to as immobilized) biological components have found applications in a variety of industries from manufacturing to medical diagnostics and therapeutics. Specific examples in the food and pharmaceutical industries include glucose isomerase, which is used for the conversion of glucose to fructose and immobilized penicillin acylase for the preparation of derivatives of penicillin. Smaller scale applications involve materials attached to magnetic beads to separate target materials from a broad mixture for diagnostic devices. Finally, many pharmaceuticals, intended for oral administration, are entrapped or encapsulated. It's expected that more applications for crosslinked biological components will be developed in the future.

One of the primary advantages of crosslinked biological components is that they can be readily separated from a solution either permitting reuse or to enhance the concentration of a target substrate. For example, immobilized enzymes can be applied in a packed column with the reactant solution pumped through the packed column to affect a desired chemical conversion, generally by the time the solution leaves the column. In such a process, the immobilized enzymes can be used multiple times at high concentrations to achieve advantageous usage of the enzymes. In another case, bacteria-specific antibodies are crosslinked to a magnetic bead which is then added to a medical sample. The antibodies bind to a specific bacterial target, and when a magnet is applied, all the particles and attached bacteria are concentrated in one location enabling a more accurate and precise analysis. The use of biological components in a digestive environment is limited by both the acidic conditions and the presence of proteases and other digestive enzymes which act to break down and/or deactivate the desired properties of the biochemical components. For pharmaceuticals, this limitation is frequently overcome by coating the biological materials with a sacrificial layer to keep them protected from the harsh digestive environment for as long as necessary. For example, gel capsules are used to protect medications from the aggressive environment of the stomach on their way to the intestine, where they will be released and absorbed into the bloodstream. This solution, distinct from and inferior to the claimed invention, assumes the purpose of the biological materials is not to be active throughout the entire digestive environment. However, there are situations in which it is desirable for biological component to be active and/or functional throughout the entire digestive environment, for example, when a poison or toxic substance is ingested. What is needed for these situations is an alternative biochemical component that enables both reactive and/or sorbent activity throughout an entire digestive system. The current disclosure addresses these needs.

SUMMARY

To assist in fully understanding Applicant's disclosure, the following glossary of terms is provided. The terms are intended to be illustrative, and not limit the full range of Applicant's disclosure.

Glossary of Terms

Biological components generally include, but are not limited to cells, cell parts, and cell components. Cell parts generally refer to structural parts of cells, whereas cell components generally refer to a chemical component of a cell, such as for example an enzyme.

Examples of biological components include, but are not limited to:
  Enzymes, including but not limited to trypsin, glucose oxidase, chymotrypsin, lysozyme, pepsin, lipase, amylase, lactase, urease, phytase, xylanase, beta-glucanase, cellulases, hemicellulases, pectinases, fumonisin esterase, caboxylesterase, aminotransferase, Phenylalanine hydroxylase, papain, halohydrin dehalogenase, alpha galactosidase, bromelain, catalase, collagenase, pectinase, beta galactosidases, beta glycosidases, epoxidase, lactonohydrolase, lactonase, carboxypeptidase, and carboxylesterase;
  Bacteria, including, but not limited to *Lactobacillus, Lactococcus, Bifidobacterium*, and *Propionibacterium;*
  Yeast/Fungi, including but not limited to Saccharomyces, Aspergillus, Trichosporon;
  Algae, including, but not limited to Euglena, Oscillatoria, Chlamydomonas, Scenedesmus, Chlorella, Nitzschia, Navicula and Stigeoclonium;
  Antibodies;
  Aptamers;
  DNA; and
  RNA.

Support matrix refers to one or more substances used to form a particle to impart mechanical and functional stability upon a biological component that can include within it, crosslinkers, reactive polymers, support materials, and a biomass. Support materials can be inorganic, organic, and combinations thereof.

Enhanced property refers to a property associated with a second substance having a magnitude greater than the magnitude of the same property associated with a related first substance. One example of an enhanced property involves a property associated with a crosslinked biological component having a magnitude greater than the magnitude of a corresponding property associated with the free biological component.

Conditions refer to an environment in which the magnitude of properties are determined. Conditions include, but are not limited to parameters such as temperature, pH, aqueous media, non-aqueous media, oxidative environment, reductive environment, hydrolytic environment, concentration and the like.

Substantially the same conditions refer to conditions that are the same or which may not be precisely the same, but which are so similar that one skilled in the relevant field would not expect the conditions to affect the magnitude of the properties exhibited.

Reactivity is a property associated with chemical substances that refers to the ability of the substance to promote a given chemical reaction or process. The reaction or process can involve a chemical transformation to form or decompose a product. The amount of product produced or decomposed during a specific time period is one measure of a substance's reactivity. Continued reactivity under specified conditions is a measure of a substances stability under those conditions.

Sorbency refers to the ability of a substance in contact with an environment to adsorb or absorb a component sufficiently to reduce the impact that component has on the environment (e.g. reducing the concentration of the component in the environment).

Enhanced reactivity refers to a comparison of the magnitude of a measure of reactivity associated with a second substance to the magnitude of the same measure of reactivity associated with a related first substance, where the magnitude of reactivity associated with the related second substance is greater, or enhanced.

Enhanced sorbency refers to a comparison of the magnitude of a measure of sorbency associated with a second substance to the magnitude of the same measure of sorbency associated with a related first substance, where the magnitude of sorbency associated with the related second substance is greater, or enhanced.

Stability refers to a substance's ability to resist change or decomposition over a period of time in a given environment under specific conditions. For example, the maintenance of a substance's melting point or the maintenance of a substance's isoelectric point over a period of time while maintained in an adverse environment (an environment that would cause physical or chemical changes to a substance) would be a measure of the substance's stability under the specified conditions. Similarly, maintenance of a substance's reactivity under specified conditions would also be a measure of the substance's stability under the specified conditions.

Enhanced stability, as used herein involves a measure of the enhanced reactivity or enhanced sorbency measured after a period of time under a specified adverse condition.

Enhanced stability to continued exposure to a digestive fluid refers to a material's enhanced stability where the adverse condition involves continued exposure to a digestive fluid.

Biomass material refers to material produced by a biological source such as microorganisms, plants, and/or other living organisms such as mollusks, insects, or crustaceans, or portions of organisms such exoskeletons and/or shells (both organic and mineral-based). Such materials may be mechanically processed (grinding, pulverizing, and the like). For some embodiments, the biomass materials can be chemically processed or treated, whereas for other embodiments, the biomass materials are cannot chemically treated, processed, or transformed from their original state.

Synthetic organic material refers to organic materials which are man-made organic compounds created through industrial or laboratory synthesis.

Digestive condition refers to a condition experienced within an organism's digestive system including, but not limited to an enzyme deficiency, the presence of a poison, the presence of a toxin, the presence of a toxin producing bacteria, the presence of a toxin producing fungi and the presence of a toxin producing algae.

Applicant's Claimed Material

A range of biological components can be crosslinked or immobilized as described herein. For purposes of illustration, the immobilization of the enzymes trypsin, lysozyme, and glucose oxidase, and of *Lactobacillus casei* are described in detail below. Their immobilization according to the method(s) disclosed herein can and have produced immobilized biological components having:

enhanced stability over a wide range of pH, enhanced resistance to aggressive conditions, such as high concentrations of protease, more retained functionality after exposure to aggressive environments than the original biological component used in its manufacturing;

enhanced activity both inside and outside of the digestive environment;

enhanced stability both inside and outside of the digestive environment; and sorbent properties in digestive fluids (the non-encapsulated form).

The crosslinked forms of Applicant's claimed material including a biological component such as trypsin and glucose oxidase can take on a variety of physical forms such as a fine powder, a pellet, or a coating, depending on the application's requirements. Certain embodiments of the crosslinked and supported biological component involve a solid support matrix to which the component is chemically bound. This chemical binding takes place by chemically joining the active materials to the support matrix through covalent bonds using a crosslinker.

Surprisingly, the immobilized biological components in the form of trypsin and glucose oxidase prepared according to the methods described herein demonstrate the following unexpected advantages:

The immobilized trypsin, lysozyme, glucose oxidase, and *L. casei* show greater resistance to degradation from acid pH conditions than native enzyme;

The immobilized trypsin, lysozyme, glucose oxidase, and *L. casei* demonstrate resistance to degradation from protease digestion; and The immobilized trypsin and lysozyme demonstrate enhanced reactivity compared to the native enzyme under conditions typically used for enzymatic transformations.

The specific examples provided below demonstrate the methods for preparing and utilizing immobilized forms of trypsin, glucose oxidase. In addition, these methods can be used to prepare a range of claimed materials based on a range of biological components. The methods provided can be utilized to prepare a wide range of different crosslinked or immobilized biological components, including but not limited to:

Enzymes, including but not limited to trypsin, glucose oxidase, chymotrypsin, lysozyme, pepsin, lipase, amylase, lactase, urease, phytase, xylanase, beta-glucanase, cellulases, hemicellulases, pectinases, fumonisin esterase, caboxylesterase, aminotransferase, phenylalanine hydroxylase, and papain;

Bacteria, including, but not limited to *Lactobacillus*, and *Lactococcus*;

Yeast/Fungi, including but not limited to Saccharomyces, Aspergillus, and Trichosporon;

Algae, including, but not limited to Euglena, Oscillatoria, Chlamydomonas, Scenedesmus, Chlorella, Nitzschia, Navicula and Stigeoclonium;

Antibodies;

Aptamers;

DNA; and

RNA.

Preferred embodiments of Applicant's invention involve materials comprising non-encapsulated forms of a crosslinked biological component covalently bonded to a support matrix. The crosslinked biological component is covalently bonded to a crosslinking agent; the support matrix includes a polyamine and at least one support material. For some embodiments, the biological component can function as a support material. Biological components include, but are not limited to enzymes, bacteria, yeast, fungi, algae, antibodies, aptamers, DNA's, and RNA's. Preferred biological components include trypsin, glucose oxidase, non-living microbial cells, microbial cell parts, antibodies, and enzymes. The claimed materials have at least one enhanced property compared to the corresponding property of the non-crosslinked biological component determined under substantially the same conditions; where the property and enhanced property each has a magnitude, and where the magnitude of the enhanced property of the material including the biological component is at least about 1.1 times greater than the magnitude of the corresponding property of the non-crosslinked biological component under the substantially the same conditions. Certain embodiments of Applicant's claimed material can exhibit at least one enhanced property whereas other embodiments can exhibit at least two enhanced properties.

Typical enhanced properties include, but are not limited to enhanced reactivity, enhanced stability of the material to the continued exposure to digestive fluids, enhanced sorbency, and combinations thereof. The magnitude of enhanced properties exhibited by the claimed materials have ranged from at least about 1.1 times to as much as at least 7 times the magnitude of the corresponding non-crosslinked biological material when exposed to the same conditions. For example, enhanced reactivities have ranged from at least about 1.1, to at least about 2, to at least about 3, and to at least about 4. The magnitude of enhanced reactivities for certain embodiments of the claimed materials have ranged from about 1.1 to about 2, from about 2 to about 3, and from about 3 to about 4. The enhanced stability to the continued exposure to digestive fluids measured after exposure to digestive fluids have ranged from at least about 2, at least about 3, at least about 5, and at least about 7. The magnitude of enhanced stabilities for certain embodiments of the claimed materials have ranged from about 2 to about 3, from about 3 to about 5, and from about 5 to about 7. Enhanced sorbencies have ranged from at least about 1.1, at least about 1.3, and at least about 1.5. The magnitude of enhanced sorbencies for certain embodiments of the claimed materials have ranged from about 1.1 to about 1.3, from about 1.3 to about 1.5, and from about 1.5 to about 2.

Suitable support materials include, but are not limited to inorganic support materials such as, for example, manganese oxides, iron oxides, silica, glass, ceramic, gold, clay, metal oxides, and combinations thereof, and organic materials, such as, for example, a biomass material, a synthetic organic material, and combinations thereof. Suitable polyamines include, but are not limited to polyethylenimine, polypyrrole, chitosan, a protein, gelatin, and combinations thereof.

Suitable crosslinking agents include, but are not limited to a triazine, a dialdehyde, genipin, disuccinimidyl suberate, an organic diacid, dimethyl pimelimidate, cyanuric chloride, hexamethylene diisocyanate, diimidoester, di(n-hydroxysuccinimide ester), diisocyanate, and a combination thereof.

The claimed materials have demonstrated enhanced stability in a range of digestive fluids, including, but not limited to saliva, gastric fluid, pancreatic fluid, intestinal fluid, and bile. Enhanced stability to the continued exposure to digestive fluids as evidenced by their maintaining at least some properties for at least 4 hours. Stabilities for periods of 24 hours can be achieved in some digestive fluids.

A still further embodiment of Applicant's claimed invention involves a method for treating an organism having a digestive condition including, but not limited to an enzyme deficiency, the presence of a poison, the presence of a toxin, the presence of a toxin producing bacteria, the presence of a toxin producing fungi, and the presence of a toxin producing algae, where the method includes administering an effective amount of a non-encapsulated form of a crosslinked biological component covalently bonded to a support matrix described above. Oral administration is a preferred manner of administration. Preferred organisms include members of the animal kingdom, preferably mammals, and most preferably humans.

DETAILED DESCRIPTION

For the purposes of promoting an understanding of the principles of the claimed technology and presenting its currently understood best mode of operation, reference will now be made to the embodiments described and specific language will be used to describe the same. It will nevertheless be understood that no limitation of the scope of the claimed technology is thereby intended, with such alterations and further modifications in the illustrated claimed material and such further applications of the principles of the claimed technology as illustrated therein being contemplated as would normally occur to one skilled in the art to which the claimed technology relates. The following description describes the preparation of specific embodiments of Applicant's claimed material, and demonstrate examples of the materials exhibited enhanced properties.

Crosslinked and Supported Reactive and Sorbent Materials Introductory Comments:

The materials produced in the following process examples of this invention involve selected biological components crosslinked to a biodegradable, organic material. It is envisioned that a still broader variety of support material discussed above will also demonstrate the improved functionality shown. The process involves preparing the support material, adding the crosslinker, adding the reactive/sorbent material and allowing the components to chemically bind together. The resulting material can then be transformed into the final physical form suited for the intended application. Four overall methods for preparing the claimed materials are provided.

Method 1: Dried Batch Pellet/Powder Process:

Support materials such as, for example, fermentation mycelium (about 15% of product mass) and chitosan (about 60% of product mass), are mixed in DI water at room temperature for about 15-30 minutes or until well dispersed. A crosslinker, such as, for example, succinic acid or glutaraldehyde, is added dropwise to the solution and the solution allowed stirring for about 30 minutes. The provided biological component, e.g. trypsin, glucose oxidase or other biological component, (about 25% of product mass) is dissolved or dispersed in chilled (about 4° C.) DI water and the chilled solution added to the dispersed mycelium/chitosan mixture. Following this addition, additional crosslinker can be added dropwise up to a total addition of about 3 wt. % vs buffer volume. The solution is mixed for about 30-240 minutes at temperatures between about 4° and about 30° C. Following the mixing process, the slurry is centrifuged and the precipitate collected. The precipitate can be washed with DI water or buffer solution and further centrifuged for purification as necessary. Following any wash steps the precipitate is spread out on a drying plate and dried overnight. Dried material is collected and ground to the necessary specifications. As a finishing step, the powder obtained can be reconstituted into pellets or any other final product shape required.

Method 2: Freeze Dried Batch Pellet/Powder Process:

Chitosan (about 2 wt. %) is added to DI water and mixed until well dispersed. An organic acid such as acetic acid, succinic acid, or citric acid at about 2% by volume, is added to the dispersion and mixed until the solution is mostly clear. The clearing process can be accelerated by heating the dispersion. Fermentation mycelium or other support materials can be added at this point if desired. The material is cooled to room temperature, and the desired mass of biological component is dissolved in chilled (about 4° C.) water (DI water at a pH between about 3 and about 7) and added to the room temperature chitosan mixture. The reaction mixture is stirred while a crosslinking material (succinic acid, glutaraldehyde, or the like) is added. The concentrated mixture is frozen and lyophilized to provide a dry solid which is collected and ground to a fine powder. To make the lyophilization step more efficient, excess water can be removed from mixture by processes including, but not limited to, vacuum evaporation or filtration prior to freezing.

Method 3: Acid/Base Precipitation-Based Pellet Process:

Chitosan (about 2 wt. %) is added to DI water and mixed until well dispersed. An organic acid, such as acetic acid, succinic acid, or citric acid, at about 2% by volume, is added to the dispersion and mixed until the solution is mostly clear. Clearing can be accelerated by heating the dispersion. Fermentation mycelium or other support materials may be added at this point if desired. The material is cooled to room temperature, and the desired mass of functional material is dissolved in chilled (about 4° C.) water (DI water at a pH between about 3 and about 7) and added to the room temperature chitosan mixture.

A bath solution consisting of about 24% ethanol and about 76% 1M aqueous NaOH is prepared. The product mixture is added dropwise to the bath solution with gentle stirring. Pellet size can be controlled by the flow rate of the product mixture and the size of the dispenser. The dispensing system should be sized to accommodate any solids present in the enzyme containing mixture. Solids formed in the bath solution are isolated and gently washed with DI water until the pH of the wash effluent is about 7. Solids obtained are suspended in a buffer solution at pH of about 7 and a crosslinker, such as glutaraldehyde, is added to the suspension at about 3% vs. the buffer volume and allowed to crosslink the suspension's components. After allowing time for the crosslinker to react, the solid is washed with DI water to remove excess unreacted crosslinker and buffer salts. Optionally, the pellets may be rinsed with a buffer solution containing additional biological component or another material to react with unbound surface-exposed crosslinker and passivate active crosslinker sites. The washed solid can then be stored in buffer solution, or separated and dried using conventional methods such as, for example, air drying, oven drying, desiccation, or freeze drying.

Method 4: Emulsion-Based Pellet Process:

Chitosan (about 2 wt. %) is added to DI water and mixed until well dispersed. An organic acid, such as acetic acid, succinic acid, or citric acid, at about 2% by volume, is added to the dispersion and mixed until the solution is mostly clear. Clearing can be accelerated by heating the dispersion. Fermentation mycelium or other support materials may be added at this point if desired. The material is cooled to room temperature, and the desired mass of functional material is dissolved in chilled (about 4° C.) water (DI water at a pH between about 3 and about 7) and added to the room temperature chitosan mixture.

A non-aqueous bath solution containing one or more organic oils or solvents, such as sunflower oil, paraffin oil, hexane, or hexadecane, is prepared with surfactant and stirred to form an emulsion. The concentration of the surfactant is adjusted such that it will produce an emulsion of particles, instead of a complete phase separation when the aqueous product solution is added. The mixture is added dropwise to the bath solution under rigorous stirring to facilitate the formation of a solid in the form of small pellets. A crosslinker is incrementally added to the mixture up to about 3% by wt. of the particle mass and allowed to react crosslinking the pellet's components. The resulting crosslinked pellets are washed to remove oils, solvents, surfactants, and unreacted material. Optionally, the pellets may be rinsed with a buffer solution containing additional functional material or another material to react with unbound surface-exposed crosslinker and passivate active crosslinker sites. The pellets obtained are collected, washed, and stored in buffer solution, or separated and dried using conventional methods such, for example, air drying, oven drying, desiccation, or freeze drying.

Testing Procedures

Enzyme Activity Measurements:

Advantages of immobilizing the enzyme described herein include enhanced stability of the enzyme with respect to exposure to a range of elevated temperatures; and enhanced activity over a broad range of pH conditions. The activity of the immobilized enzymes prepared herein was tested to identify these advantages.

Trypsin cleaves peptide chains primarily at the carboxyl side of the amino acids, lysine or arginine, except when either is followed by proline. This process can be measured by monitoring the cleavage of Nα-Benzoyl-L-Arginine Ethyl Ester (BAEE). One BAEE unit is defined as the amount of enzyme that will produce a change in absorbance at 253 nm of 0.001 per minute with BAEE as a substrate at pH 7.6, 25° C., in a reaction volume of 3.20 mL.

Glucose oxidase catalyzes the oxidation of β-D-glucose to D-glucono-δ-lactone with the concurrent release of hydrogen peroxide. In the presence of peroxidase (POD) this hydrogen peroxide ($H_2O_2$) enters into a second reaction involving p-hydroxybenzoic acid and 4-aminoantipyrine with the quantitative formation of a quinoneimine dye complex which is measured at 510 nm. One unit of glucose oxidase is defined as the amount of enzyme that generates 1.0 mmole of $H_2O_2$ per minute at 37° C.

Lysozyme is an antimicrobial enzyme that is found in a wide variety of organisms. It performs its antimicrobial function by hydrolyzing the beta-glycosidic linkages between N-acetylmuramic acid and N-acetyl glucosamine in the peptidoglycan of bacterial cell walls and can also bind polymers of N-acetyl glucosamine. The activity of a lysozyme sample is measured by the rate of lysis of *Micro-*

*coccus lysodeikticus* cells. One unit is defined as a change in absorbance of 0.001 per minute, measured at 450 nm, pH 7.0, and 25° C.

Aflatoxin Concentration Measurements:

Aflatoxin $B_1$ is a mycotoxin produced by *Aspergillus flavus* and *Aspergillus parasiticus*. It is a common contaminant in a variety of agricultural products such as corn and other grains, and is considered of the most toxic of the aflatoxins. Aflatoxin $B_1$ can be detected by fluorescence as it has a maximum absorbance around 360 nm with an emission wavelength of 425 nm. Alternatively, there are a number of commercial test kits available that utilize enzyme-linked immunosorbent assay (ELISA) or competitive lateral flow assay (LFA) techniques to identify the concentration of aflatoxin $B_1$ in a sample. To evaluate the absorptive properties of a target material, a known mass of material was added to a 100 ppb solution of aflatoxin $B_1$ and mixed for 2 hours. After mixing the solution was centrifuged and a sample of the supernatant was taken. This sample was diluted to 65% v/v ethanol. The final mixture was tested using the techniques described above to determine the remaining aflatoxin $B_1$ concentration.

Stability in Digestive Environment:

It has now been surprisingly and unexpectedly discovered that the immobilization process can imbue resistance to the biological component against the detrimental effects of exposure to digestive conditions such as low pH (~2-4) and the presence of digestive enzymes such as protease (e.g. pepsin). The process is non-specific and has demonstrated the ability to allow trypsin and glucose oxidase to maintain appropriate functionality after exposure to a digestive fluid or environment. For this test, soluble and immobilized materials were immersed in a 6 mL solution containing 7500 U of pepsin at a pH 3 and incubated at 40° C. for 40 minutes, simulating mammalian stomach conditions. At the end of the test time the digestion solutions were immediately chilled in an ice bath to minimize the activity of the pepsin. For the soluble enzyme, a sample was taken from the digestion reaction and applied to the particular assay described previously. As pepsin activity is low at pH over 7 while trypsin is significantly more active and each enzyme cleaves different bonds, it was not expected that any pepsin transferred into the trypsin assay would interfere with the final assay results. Glucose oxidase reacts by combining sugar and oxygen and no component directly interacts with pepsin. Lysozyme only reacts with bacterial cell wall components, and will not degrade pepsin. Alfatoxins, will degrade at pH's under 4 such as those under the conditions tested, but this degradation is slow. For immobilized material, any solid component was separated from the pepsin solution by centrifugation and then washed with DI water. The immobilized material was then assayed utilizing standard assay procedures. If no solid component was recoverable due to small particle sizes, a sample from the digestion reaction was taken and tested similarly to the soluble enzyme testing. Results from this testing with trypsin are shown in Table 1, glucose oxidase in Table 2, and lysozyme in Table 3. Table 4 contains results of testing immobilized absorptive materials under these conditions.

TABLE 1

Trypsin activity following simulated digestive exposure

| Trypsin Activity [BAEE U/mg enzyme] | Pre-Exposure | Post Exposure | Retained Activity | Relative Activity |
| --- | --- | --- | --- | --- |
| Soluble Trypsin | 5270 | 395 | 7.5% | 1.0 |
| Immobilized Trypsin Powder (Method 2) | 5024 | 2805 | 55.8% | 7.4 |
| Immobilized Trypsin Pellet (Method 3) | 2196 | 1051 | 47.9% | 6.4 |

TABLE 2

Glucose Oxidase activity following simulated digestive exposure

| Glucose Oxidase Activity [U/mg enzyme] | Pre-Exposure | Post Exposure | Retained Activity | Relative Activity |
| --- | --- | --- | --- | --- |
| Soluble Glucose Oxidase | 81.6 | 9.3 | 11.3% | 1.0 |
| Immobilized Glucose Oxidase Pellet (Method 4) | 7.6 | 6.4 | 85.9% | 7.6 |

TABLE 3

Lysozyme activity following simulated digestive exposure

| Lysozyme Activity [U/mg enzyme] | Pre-Exposure | Post Exposure | Retained Activity | Relative Activity |
| --- | --- | --- | --- | --- |
| Soluble Lysozyme | 18160 | 11600 | 63.7% | 1.0 |
| Immobilized Lysozyme Powder (Method 2) | 23500 | 20900 | 88.9% | 1.4 |

TABLE 4 ppb of aflatoxin Bi absorbed per mg of sorbent material following simulated digestive exposure

| Aflatoxin $B_1$ Absorbed [ppb/mg sorbent material] | Pre-Exposure | Post Exposure | Retained Activity | Relative Activity |
| --- | --- | --- | --- | --- |
| Untreated Sorbent | 1.61 | 0.43 | 26.4% | 1.0 |
| Immobilized Sorbent Powder (Method 1) | 1.80 | 0.89 | 67.7% | 2.6 |

As can be seen from these results, although there is degradation in the measured activity of each of the enzymes tested, immobilized materials can retain 6 to more than 7 times the activity of the soluble enzyme after a simulated digestive exposure. The results also show that the immobilization process does not always deliver the same results in terms of the pre-exposed material's activity. At even longer periods of contact with the digestive fluids, as long as 4 hours, some enzyme activity was retained by the claimed material.

A similar test can be used to simulate mammalian intestine conditions. Soluble and immobilized materials are immersed in a 10 mL, 40 mM sodium phosphate solution containing 0.5 mg/mL pancreatin (from porcine pancreas) at a pH of 6.4. At the end of the test period samples were either immediately tested for activity, or chilled in an ice bath to reduce the activity of digestive enzymes. For soluble samples, evaluation tests were performed directly on samples from the digestion assay as described previously. The only significant difference in this testing approach is with respect to materials using trypsin, as pancreatin contains trypsin. In this case a control test of the intestinal material is used as a baseline to subtract out the activity of the additional trypsin in pancreatin. For immobilized material, any solid component was separated from the pepsin solution by centrifugation and then washed with DI water. The immobilized material was then assayed utilizing standard assay procedures. If no solid component was recoverable due to small particle sizes, a sample from the digestion reaction was taken and tested similarly to the soluble enzyme testing. Results from testing samples versus intestinal conditions are shown in Tables 5, and 6.

TABLE 5

Lysozyme activity following simulated digestive exposure

| Lysozyme Activity [U/mg enzyme] | Pre-Exposure | Post Exposure | Retained Activity | Relative Activity |
|---|---|---|---|---|
| Soluble Lysozyme | 18160 | 19330 | 106.5% | 1.0 |
| Immobilized Lysozyme Powder (Method 2) | 23500 | 27240 | 115.9% | 1.1 |

TABLE 6 ppb of aflatoxin $B_1$ absorbed per mg of sorbent material following simulated digestive exposure

| Aflatoxin $B_1$ Absorbed [ppb/mg sorbent material] | Pre-Exposure | Post Exposure | Retained Activity | Relative Activity |
|---|---|---|---|---|
| Untreated Sorbent | 1.61 | 1.23 | 76.4% | 1.0 |
| Immobilized Sorbent Powder (Method 1) | 1.80 | 1.59 | 88.4% | 1.2 |

Increase in Enzyme Activity:

Immobilized enzymes typically have reduced activity compared to the native enzyme. This reduction of activity is believed to be due to the enzyme's random orientation in the immobilized environment and to the binding of crosslinker to functional groups that block or otherwise hinder the ability of a substrate to enter into an enzyme's active site and react. It was surprisingly and unexpectedly discovered that the activity of the crosslinked and supported trypsin exhibited greater enzymatic activity on a per gram enzyme basis than the soluble/untreated parent enzyme. Table 7, provided below, illustrates the measured activity of soluble trypsin compared with the activity of three immobilized versions of the same trypsin and Table 8 shows the measured activity of crosslinked and supported lysozyme versus the same soluble lysozyme.

TABLE 7

Increased Enzyme Activity with Immobilization

| | BABE U/mg enzyme | % activity of soluble enzyme | Relative Activity |
|---|---|---|---|
| Soluble Trypsin | 12,609 | 100% | 1.00 |
| Trypsin-Method 1 | 57,261 | 454% | 4.54 |
| Trypsin-Method 1 | 38,779 | 308% | 3.08 |
| Trypsin-Method 2 | 15,917 | 127% | 1.27 |
| Trypsin-Method 2 | 17,404 | 138% | 1.38 |

TABLE 8

Increased Enzyme Activity with Immobilization

| | U/mg enzyme | % activity of soluble enzyme | Relative Activity |
|---|---|---|---|
| Soluble Lysozyme | 18160 | 100% | 1.00 |
| Lysozyme-Method 1 | 25460 | 140.% | 1.40 |

Because the immobilization of enzymes typically results in a reduction of enzyme's activity as noted above, this increase in activity was completely unexpected. Generally immobilized enzymes show reduced activity, typically never equaling the activity of the native enzyme.

Preparation of Specific Claimed Materials

Example 1: Immobilized Enzyme Production by Method 1

15 g of *A. Niger* mycelium and 0.9 g of chitosan and were dispersed in 200 mL of 100 mM phosphate buffer (pH 7.4) by mixing in a water bath at 6° C. 0.9 mL of a 6.0% w/v succinic acid solution was added dropwise and the mixture was stirred for 120 min. A chilled 100 mL solution of 0.1 g trypsin in 1 mM HCl was prepared and added to the reaction and allowed to mix for 90 minutes. 0.9 mL of a 6.0% w/v succinic acid solution was again added to the reaction mixture and the material was again allowed to mix for 90 minutes. Crosslinked material was separated by centrifugation and spread out on a drying plate and allowed to air-dry for 24 hours. Dried materials were ground using a ball mill, and stored at 4° C. until tested.

Example 2: Crosslinked and Supported Absorbent Cell Production by Method 1

*Lactobacillus casei*. were grown in flasks in a shaking incubator using MRS broth for 72 hours at 30° C. and 250 RPM. Cells were harvested via centrifugation at 2000×G for 5 min. Cell pellets were weighed and re-suspended in 100 mM sodium phosphate buffer (pH 7.4). Chitosan was added at 12.5 wt. % and cellulose at 5 wt. % both with respect to the mass of the cell pellet. The solution was mixed by overhead mixing until well dispersed. 150 mg of glutaraldehyde was added dropwise to the solution and it was mixed for one hour. Crosslinked materials were collected by centrifugation. Collected solids were dried overnight at 30° C. and subsequently ground to a powder using a ball mill. Powders were stored at 4° C. until needed.

Example 3: Crosslinked and Supported Powder by Method 2

0.4 g of chitosan and 0.1 g of cellulose are mixed into 80 mL of a 0.75% acetic acid solution. After materials are well mixed 0.4 g of succinic acid are dissolved into the solution. 0.3 g of egg white lysozyme are then mixed into the solution for 10 minutes. The prepared sample is then frozen and lyophilized. The resulting crosslinked material is collected and ground into a fine powder using a ball mill and stored at 4° C. until needed.

Example 4: Crosslinked and Supported Pellets/Powder by Method 3

4 g of chitosan was dissolved in 200 mL of a 2% acetic acid solution. After the solution clarifies 2 g of cellulose are mixed in followed by 3 g of glucose oxidase. The material is allowed to mix until all the components have been dispersed. A bath solution consisting of 24% ethanol and 76% 1M aqueous NaOH is prepared. The product mixture is added dropwise to the bath solution with gentle stirring at a rate of 40 □L/second. Formed pellets are gently washed with once with ethanol, and then washed DI water until the pH of the wash effluent reaches close to 7. The washed pellets are suspended in a 20 mM sodium phosphate buffer and glutaraldehyde is added at 3 wt % with respect to the total pellet mass. The pellets are mixed for 1 hour, and then washed with DI water to remove excess crosslinker and buffer salts. Free glutaraldehyde sites on the particles were neutralized by 25 mM ethanolamine solution. The particles are washed again and are dried in air for 24 hours. Final pellets can be used as is or ground into a powder based on the desired application.

Example 5: Crosslinked and Supported Pellets/Powder by Method 4

2 g of chitosan are dispersed in 100 mL of DI water. 2% w/v succinic acid is added to the solution and it is mixed until the chitosan particles are dissolved. 4.2 g of *A. Niger* mycelium are then dispersed into the mixture, followed but 2 g of trypsin. Once well mixed the reaction solution is added dropwise into an organic oil bath consisting of equal amounts of hexane and mineral oil, and 1.5% v/v surfactant (Tween-20). The solution is mixed rapidly and the concentration of surfactant is adjusted as needed such that the mixing produces an emulsion of particles while preventing a phase separation between the organic and aqueous phase material. After mixing for 30 minutes, glutaraldehyde is slowly added up to 3% w/w with respect to the mass of the solid material. The crosslinking reaction is allowed to run for up to 4 hours with gentle stirring. The resulting crosslinked pellets are subsequently washed with hexane, ethanol, and DI water to remove oils, solvents, surfactants, and unreacted material. The final pellets are stored in buffer solution, or separated and dried as needed.

While the claimed technology has been illustrated, and described in detail in the foregoing description, the same is to be considered as illustrative and not restrictive in character. It is understood that the embodiments have been shown and described in the foregoing specification in satisfaction of the enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

The invention claimed is:

1. A material comprising a non-encapsulated form of a biological component crosslinked and covalently bonded to a support matrix;
   wherein the support matrix includes a polyamine and at least one support material;
   wherein the biological component is an enzyme; and
   wherein the material is more active than the biological component the material was formed from, on an equivalent basis.

2. The material of claim 1, wherein the biological component is an enzyme selected from the group consisting of trypsin, glucose oxidase, chymotrypsin, lysozyme, pepsin, lipase, amylase, lactase, urease, phytase, xylanase, beta-glucanase, cellulases, hemicellulases, pectinases, fumonisin esterase, caboxylesterase, aminotransferase, Phenylalanine hydroxylase, papain, halohydrin dehalogenase, alpha galactosidase, bromelain, catalase, collagenase, pectinase, beta galactosidases, beta glycosidases, epoxidase, lactonohydrolase, lactonase, carboxypeptidase, and carboxylesterase.

3. The material of claim 1, wherein the material is at least 1.1 times more active than the biological component the material was formed from, on an equivalent basis.

4. The material of claim 1, wherein the support material is an inorganic support material selected from the group consisting of manganese oxides, iron oxides, and combinations thereof.

5. The material of claim 1 wherein the support material is an organic support material selected from the group consisting of a biomass material, a synthetic organic material, and combinations thereof.

6. The material of claim 1, wherein the polyamine is selected from the group consisting of polyethylenimine, polypyrrole, chitosan, a protein, and combinations thereof.

7. The material of claim 6, wherein the polyamine is chitosan.

8. The material of claim 1, wherein the biological component crosslinked and covalently bonded to a support matrix is crosslinked with a crosslinking agent selected from the group consisting of a dialdehyde, an organic polyacid, and a combination thereof.

9. The material of claim 8, wherein the crosslinking agent is selected from the group consisting of succinic acid, citric acid, glutaraldehyde, and combinations thereof.

10. The material of claim 1, wherein the increased activity of the material includes increased activity in the presence of a digestive fluid selected from the group consisting of saliva, gastric fluid, pancreatic fluid, intestinal fluid, and bile.

11. The material of claim 1, wherein the biological component is an enzyme, the material is a crosslinked immobilized enzyme, and the crosslinked immobilized enzyme is at least 2 times more active than the enzyme the crosslinked immobilized enzyme was formed from, on an equivalent basis.

12. The material of claim 1, wherein the biological component selected is an enzyme and the enzyme is selected from the group consisting of trypsin, chymotrypsin, lysozyme, lipase, amylase, phytase, xylanase, beta-glucanase, alpha-galactosidase, and urease.

13. The material of claim 12, wherein the biological component selected is an enzyme, and the enzyme is selected from the group consisting of trypsin and lysozyme.

14. The material of claim 1, wherein the biological component is an enzyme, the material is a crosslinked immobilized enzyme, and the crosslinked immobilized enzyme is at least 3 times more active than the enzyme the crosslinked immobilized enzyme was formed from, on an equivalent basis.

15. A method for treating an organism having a digestive condition including a condition selected from the group consisting of an enzyme deficiency, the presence of a poison, the presence of a toxin, the presence of a toxin producing bacteria, the presence of a toxin producing fungi, and the presence of a toxin producing algae the method comprising administering an effective amount of the material of claim 1.

16. The method of claim 15, wherein the material of claim 15, is administered orally.

17. The method of claim 15, wherein the organism treated is a member of the animal kingdom, and wherein the material maintains its increased reactivity through the organism's digestive system.

18. The method of claim 17, wherein the effective amount of the material of claim 1 administered to a member of the animal kingdom is administered to a mammal.

19. The method of claim 18, wherein the effective amount of the material of claim 1 administered to a mammal is administered to a human.

\* \* \* \* \*